United States Patent
Bauer et al.

(10) Patent No.: US 10,150,263 B2
(45) Date of Patent: Dec. 11, 2018

(54) TESTING ARRANGEMENT FOR CONTROLLING THE MANUFACTURING OF A COMPONENT

(71) Applicant: Airbus Defence and Space GmbH, Taufkirchen (DE)

(72) Inventors: Daniel Bauer, Durlangen (DE); Franz Engel, München (DE); Tilman Orth, München (DE); Christian Weimer, München (DE)

(73) Assignee: Airbus Defence and Space GmbH (DE)

( * ) Notice: Subject to any disclaimer, the term of this patent is extended or adjusted under 35 U.S.C. 154(b) by 113 days.

(21) Appl. No.: 15/208,106

(22) Filed: Jul. 12, 2016

(65) Prior Publication Data

US 2017/0015070 A1    Jan. 19, 2017

(30) Foreign Application Priority Data

Jul. 14, 2015 (EP) .................................... 15002081

(51) Int. Cl.
| | |
|---|---|
| *B29C 70/30* | (2006.01) |
| *G01M 5/00* | (2006.01) |
| *B29C 70/54* | (2006.01) |

(52) U.S. Cl.
CPC .............. *B29C 70/30* (2013.01); *B29C 70/54* (2013.01); *G01M 5/0033* (2013.01); *G01M 5/0075* (2013.01); *G01M 5/0091* (2013.01)

(58) Field of Classification Search
CPC ......... B29C 70/30; B29C 70/38; B29C 70/54; G01M 5/0033; G01M 5/0041; G01M 5/0075; G01M 5/0091

USPC .......................................... 156/350, 378, 379
See application file for complete search history.

(56) References Cited

U.S. PATENT DOCUMENTS

| | | | | |
|---|---|---|---|---|
| 2003/0145932 | A1* | 8/2003 | Holmes ............... | B23K 26/032 156/64 |
| 2006/0106507 | A1* | 5/2006 | Ledet ................. | G05B 19/4207 701/23 |
| 2006/0108048 | A1 | 5/2006 | Engelbart et al. | |
| 2006/0191622 | A1* | 8/2006 | Ritter .................... | G01N 25/72 156/64 |

(Continued)

FOREIGN PATENT DOCUMENTS

| | | |
|---|---|---|
| EP | 1574845 A1 | 9/2005 |
| EP | 1 783 501 A2 | 5/2007 |
| EP | 2 492 671 A1 | 8/2012 |

OTHER PUBLICATIONS

European Search Report dated Dec. 14, 2015 (EP 15002081.6).
EP 15002081.6 Search Report dated Apr. 25, 2018.

*Primary Examiner* — George R Koch
(74) *Attorney, Agent, or Firm* — Lerner, David, Littenberg, Krumholz & Mentlik, LLP

(57) ABSTRACT

A testing arrangement serves for controlling the manufacturing of a fiber reinforced component. The testing arrangement includes an inspection device with a sensor system, with the inspection device being configured to move on and/or above one or more material layer(s) and/or a surface of the component and to examine the material layer(s) or the surface with the sensor system. A device serves for automated manufacturing of a fiber reinforced plastic laminate. The device includes a forming tool, a laying head for automated laying of material layers in the forming tool as well as a testing arrangement.

12 Claims, 1 Drawing Sheet

(56) References Cited

U.S. PATENT DOCUMENTS

| | | | |
|---|---|---|---|
| 2006/0260751 A1* | 11/2006 | Lauder | B29C 70/388 |
| | | | 156/382 |
| 2007/0034313 A1 | 2/2007 | Engelbart et al. | |
| 2007/0044918 A1* | 3/2007 | Warek | B29C 70/28 |
| | | | 156/351 |
| 2007/0277919 A1* | 12/2007 | Savol | B29C 70/386 |
| | | | 156/64 |
| 2008/0055591 A1* | 3/2008 | Walton | G01N 21/8901 |
| | | | 356/237.1 |
| 2008/0169828 A1 | 7/2008 | Brady | |
| 2008/0174306 A1 | 7/2008 | Brady | |
| 2011/0285402 A1 | 11/2011 | Dorr et al. | |
| 2014/0168420 A1* | 6/2014 | Naderhirn | G01M 5/0016 |
| | | | 348/128 |
| 2014/0336928 A1* | 11/2014 | Scott | G01N 21/88 |
| | | | 701/468 |
| 2016/0375631 A1* | 12/2016 | Encinosa | B29C 33/26 |
| | | | 156/91 |

* cited by examiner

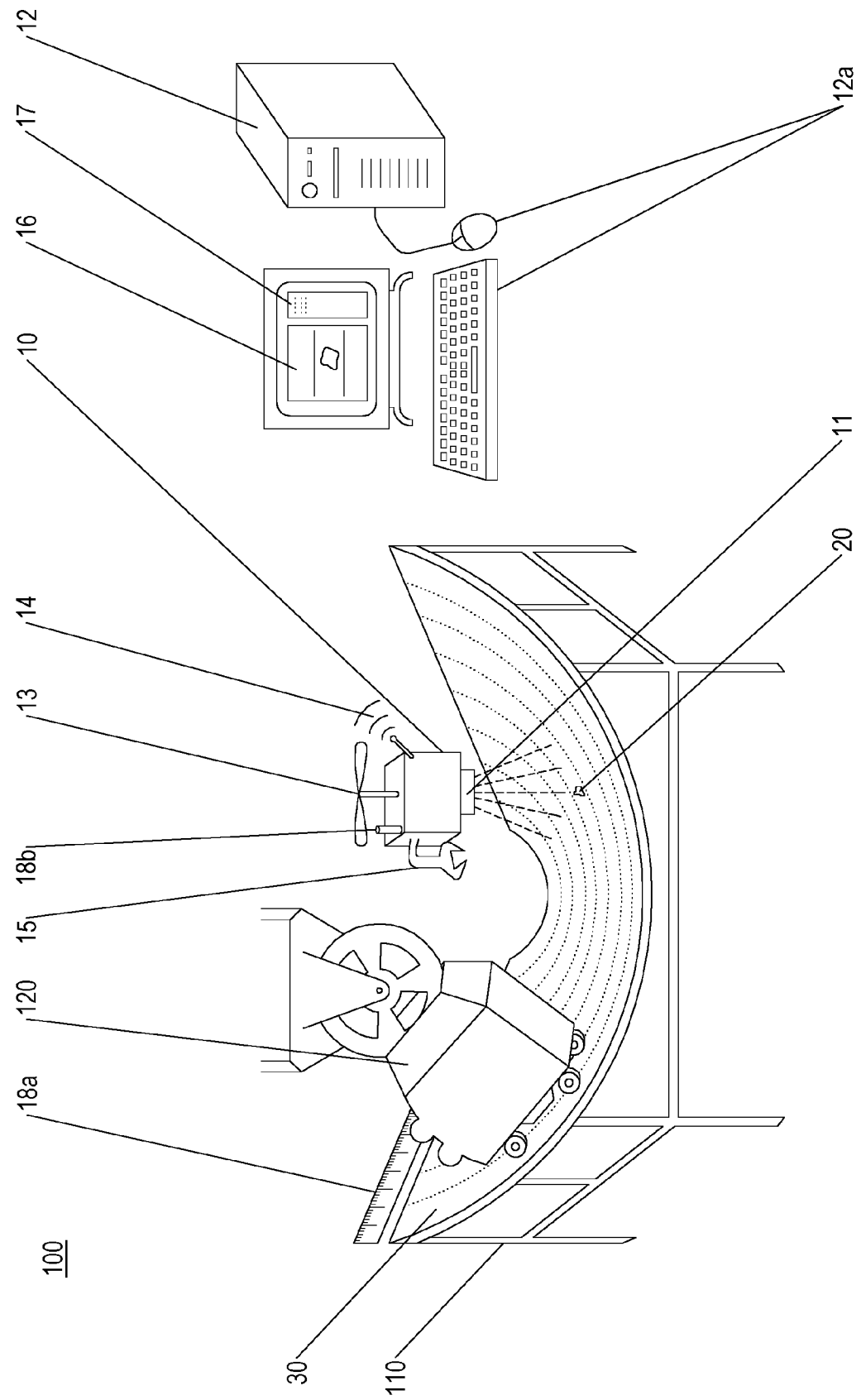

TESTING ARRANGEMENT FOR CONTROLLING THE MANUFACTURING OF A COMPONENT

FIELD OF THE INVENTION

The present invention relates to a testing arrangement for controlling fiber reinforced components during or after their manufacturing as well as to a device for automated manufacturing of a fiber reinforced plastic laminate.

BACKGROUND OF THE INVENTION

Fiber compound plastics are used in many applications. In particular, carbon fiber reinforced plastics are used in industrial components, in air and space technology, and in sports devices.

Manufacturing of the components may comprise connecting multiple units, for example by adhesive bonding or riveting. These joint locations and/or adhesive locations must be verified subsequently, which may take place in specific water ultrasonic devices.

Manufacturing of corresponding components may in particular comprise automated layer laying processes. Thereby, by means of a laying head, dry or preimpregnated fibers are subsequently laid in slim or thin strips in multiple layers in a shaping tool or forming mold.

Thereby, various defects may arise. Unwanted overlapping, gaps, or material folds may arise as a result of an incorrect laying, for example. In addition, external material may get into or onto the layers; such unwanted material may originate from the device itself (for example material abrasion in the laying head) or may intrude as contamination from the surroundings of an open tool.

For avoiding detrimental consequences, according to the prior art, laid layers are optically examined by staff members after each completed film. The forming tool can be accessed by corresponding inspectors for this purpose, partially there are also lifting systems by usage of which operators may hover over the forming tool as to inspect the laid material.

Such control mechanisms are costly, take a lot of time and often are imprecise. Additionally, in particular large control surfaces require a systematic guidance of the perspective which is often hardly to maintain so that defects may be easily overlooked. Finally, persons who enter the tool or who are guided above the material or the according hover mechanisms themselves may damage or contaminate the laid layers.

BRIEF SUMMARY OF THE INVENTION

There may be a need to provide a technique with which the manufactured components as well as automated layer laying processes can be controlled by avoiding the aforementioned drawbacks.

The testing arrangement serves to the controlling of a manufacturing of a fiber reinforced component. The testing arrangement comprises an inspection device with a sensor system. The inspection device is configured to move on and/or above one or more material layers and/or a surface of the component and to examine the material layer or layers or the surface with the sensor system.

The material layers may comprise layers which are applied during manufacturing of the component. The surface of the component may comprise an upper material layer of the manufactured component or a part of the same, in particular joints, rivets and/or adhesive areas therein.

A testing arrangement is suited in particular for controlling of automated layer laying processes. The testing arrangement enables inspection of material layers of the component during and/or after its manufacturing as laid material layers may be inspected by means of the inspection device. Thereby, its sensor system acquires one or more characteristics of scanned material layers, as for example light emission and/or heat emission. A visual search of the surface by men in or above the forming tool can thus be cancelled. In particular, the controlling can be elaborated and accelerated thereby and detrimental impacts by men and/or the lifting mechanism can be avoided.

A testing arrangement may also be utilized under conditions which are not acceptable for men, for example in an autoclave (at high temperatures), in a cooling chamber, in an unhealthy gas atmosphere and/or under water. The testing arrangement may be utilized during laying of material layers or after completing a laminate, for example within the scope of quality check.

According to a preferred embodiment, the inspection device is configured to move in a forming tool dissociated or separated from a laying head which lays material layers in an automated layer laying process. Thereby, the inspection device is preferably physically completely decoupled from the laying head, hence does not have any physical connection thereto. The inspection device may comprise its own drive and/or its on control. In particular, the inspection device is preferably configured to change its direction of movement relative to a direction of movement of the laying head.

The testing arrangement may be composed of a single one or of multiple physical units; in particular, the entire testing arrangement itself may be configured to move (with its inspection device) within the forming tool.

Alternatively, the testing arrangement may comprise, in addition to the inspection device, one or more components which can be spatially separable, for example a control unit and/or a display device and/or an operating device which is/are configured to be utilized outside the forming tool (e.g., stationary).

According to a preferred embodiment, the testing arrangement comprises at least one controlling unit. Such a controlling unit may in particular be configured to control the movement of the inspection device and/or the sensor system (for example one or more measurements which can be made by the sensor system).

According to an embodiment, the controlling unit may control the movement of the inspection device based on results of a random generator. Preferably, in this case the testing arrangement comprises sensors which are configured to acquire if the inspection device is located within a given distance to an edge of the forming tool and/or to another object in the forming tool (e.g., to a laying head as described above, to a further inspection device, and/or to a repairing device), and the controlling unit is configured to intervene the random generated movement and to cause a change of direction of the inspection device.

According to a further embodiment, the controlling unit is configured to control the movement of the inspection device along a controlled course. Thereby, the controlling unit may be configured to determine and/or correct, for example automatically depending on one or more local characteristics of laid material layers acquired with the sensor system, the course at least partially during a control process of a layer laying process carried out by the testing arrangement. Thus, the movement of the inspection device, for example, may be slowed down and/or consolidated (by increasing the course length per area) in case of noticing an anomaly. Thus, the anomaly may be examined in more detail and possibly a defect at the material layer(s) be determined, and/or the sort of and/or the extent of the defect may be determined.

A controlling unit may be configured to carry out the controlling from a stationary position; in particular, the controlling unit may thus operate from outside the forming tool.

Thereby, the controlling unit may be configured to automatically control the inspection device (in terms of its movement and/or in terms of the activities of the sensor system). Alternatively or additionally, the controlling unit may comprise an operating device and may be configured to control the inspection device depending operator inputs. Thus, this embodiment facilitates taking influence by an operator.

Alternatively, such a controlling unit may be configured to be moved together with the inspection device at and/or above the one or more material layer(s); the controlling unit may thus be coupled to the inspection device or be arranged at it.

Finally, the controlling unit may be configured to move within the forming tool dissociated from the inspection device, for example coupled to another inspection device or to a laying head of a device for automated layer laying. This is advantageous especially if the controlling unit also controls operations of the other inspection devices or of the laying head besides operations of the inspection device and, thereby, coordinates the respective operations.

The inspection device preferably comprises a drive (for example an electric motor) by means of which it moves. For movement, the inspection device may comprise wheels, stilts, at least one suspension and/or a hover mechanism. For example, a hover mechanism may comprise a suspension, e.g., a rope system and/or a rod system. A hover mechanism may further comprise a device for generating an air cushion and/or a magnetic levitation device. Alternatively or additionally, the inspection device may comprise a flight mechanism, as for example one or multiple rotors.

The examination of the material layer(s) by means of the sensor system preferably takes place locally at a multitude of positions Thereby, the inspection device may be configured to capture images of several positions of the laid material layer(s). The images (e.g., single frames or continuous capturing in form of a film) may be shown to an operator at a display device (e.g., a monitor) for evaluation. Alternatively or additionally, the testing arrangement may be configured to evaluate the images in an automated manner, for example by comparison with image patterns.

The sensor system may comprise one or multiple sensors (of similar and/or of different type). The examination of the material layer(s) or of the surface of the component by means of the sensor system preferably comprises capturing of one or more local characteristics of the material layer(s) or of the surface at multiple positions. Such a characteristic may thereby relate to a surface quality and/or material quality.

According to a preferred embodiment, the sensor system is configured to apply one or multiple of thermography method, laser light sectioning method, stray light method, laser time-of-flight measurement, image recognition, pattern recognition, magnetic resonance method, triangulation method to examine the laid material layer(s) or surface.

The testing arrangement is preferably configured to detect possible local defects, i.e., local deviations from defined target characteristics from the characteristics of the laid material layer(s) or surface captured by the sensor system;

the identification may be carried out by an analyzing unit which may be comprised by the testing arrangement and which may be arranged on or at the inspection device or may be dissociated from the same. The analyzing unit may for example be configured to compare characteristics acquired by the sensor system in form of measurement data with data of a database. A deviation of the measurement data from the data of the database may be interpreted as a defect of the laid material layer(s).

According to a preferred embodiment, the testing arrangement is configured to generate at least one optical and/or acoustical signal and/or to stop the layer laying process when finding a defect. This enables to an operator of the tool facility to cancel a manufacturing process and to restart it, if necessary, or to take appropriate countermeasures, for example by removing a dirt element or by filling a gap or whole with a filling material.

Alternatively or additionally, the testing arrangement may be configured to mark a defect on the laid material layer(s) on finding it and/or to register data of a position of the defect, for example to store said data. The defect may then be found and cleared later on. This embodiment facilitates, in particular, an advantageous process organizational clearing of defects.

The inspection device may thereby be configured to graphically label a found defect as to mark it, for example to apply a color marking and/or an adhering marking. Alternatively or additionally, the inspection device may be configured to illuminate the defect or to hold at the defect and thus serve as marking element. Furthermore, the testing arrangement may then trigger an image capturing (e.g., a photo shoot or a computer aided (virtual) image enhancement (augmented reality)) with the inspection device as a marking point. Thus, the position of the defect may be stored and later on (e.g., during a repairing step) again found automated or by an operator; alternatively or additionally, the testing arrangement may be configured to convert the position of the defect in coordinates based on the captured image.

The inspection device may be configured to fix a defect itself, for example to carry out corrections of the laid material layers and/or to remove unwanted elements. For this purpose, the inspection device may comprise one or multiple actuator(s), for example a knife, at least one scissors, at least one magnet, laser, vacuum element and/or gripper and/or at least one spray nozzle, e.g., for additional matrix material.

This embodiment may make a human interaction, in particular a human entering into the forming tool, dispensable. Thereby, the manufacturing process may be accelerated as well as the risk of repeated contamination or damage be reduced.

Finally, the inspection device may be configured to, in case of finding an anomaly or a defect, call a repairing device and/or another inspection device which is likewise being moved or standing by in the forming tool. The other inspection device may here comprise another sensor system compared to the (first) inspection device, for example a more detailed one or one based on another principle. Thus, additional knowledge about the anomaly or the defect may be gained.

According to a preferred embodiment, the testing arrangement is configured to capture of which type a recognized defect is, if there is locally, for example a whole and/or a crack in the strip, or a gap between strips, a folding of a strip and/or an unevenness of the surface (e.g., as a result of air bubbles under a layer or as a result of unwanted objects (e.g., dust elements)). Alternatively or additionally, the testing arrangement may be configured to capture if there are locally interior air bubbles, for example, and/or it may capture a degree of dryness of the material.

The testing arrangement may be configured to capture the extent of a detected defect. Depending on a type and/or an extent of the detected defect, the testing arrangement may further be configured to make a selection from a multitude of actions (as, for example, those mentioned above) which are possible when finding a defect.

According to an advantageous embodiment, the testing arrangement comprises a position system for determining a position of the inspection device in the forming tool. Thus, the respective current position of the inspection device in the forming tool can be determined preferably continuously or at determined points of time (e.g., in regular intervals).

The position system may comprise an arrangement for generating signals (e.g., sound waves or electromagnetic waves which may be modulated) as well as a receiving unit and an evaluating unit which may be configured to determine a current position of the inspection device by means of triangulation based on a received signal. The arrangement for generating signals and/or the receiving unit and/or the evaluating unit each may thereby be arranged at or on the inspection device and/or at one of the units dissociated from the inspection device, for example at the forming tool or outside the same. In case the arrangement for generating signals and the receiving unit are both arranged at or on the inspection device or both separated from the same, the receiving unit is preferably configured to detect reflections of emitted signals, for example signals reflected at the edge of the forming tool or at the inspection device, respectively.

Alternatively or additionally, the position system may comprise a unit for generating a guiding beam and/or a light pattern and/or a magnetic or electromagnetic field. The inspection device is then preferably configured to determine its position based on the guiding beam or the light pattern or the (electro-)magnetic field.

Alternatively or additionally, the position system may comprise one or multiple motion sensor(s) at or on the inspection device, which motion sensor(s) is/are configured to detect one or multiple movement characteristics of the inspection device (e.g., change of direction, speed). An evaluation system additionally comprised by the position system may then follow a movement of the inspection device based on the captured movement characteristics and may thereby determine respective current position data.

Finally, the position system may comprise a device for visual capturing of the forming tool with the inspection device located therein, as well as an evaluation unit which is configured to virtually apply a coordinate system to captured images and to automated determine a current position of the inspection device therefrom.

According to an advantageous embodiment, the testing arrangement comprises a display device (for example a monitor) which is configured to graphically display the results of the testing arrangement. Thereby and in particular, the forming tool may be displayed in its entirety or at least in part, wherein defects found so far may be visualized; preferably, the display device is configured to be respectively updated when finding a defect (in particular a further defect).

An operator may thus get an overview of the quality of a manufacturing process or manufactured component.

The display device may additionally comprise at least one operating element which can be used to influence the graphical representation (e.g., with regard to size, section, and/or perspective) and/or which can be used to control at least one element of the testing arrangement (e.g., the inspection device). Thus, the display device enables an operator to take influence on the manufacturing process or control process.

Preferably, the inspection device comprises means of communication by which the inspection device can communicate with other elements in a device for automated layer laying, for example with another inspection device and/or with a laying head and/or with an additionally available repairing device. Therefore, the inspection device may be configured to avoid collisions with the other inspection device and/or with the laying head, and/or to call the other inspection device or the repairing device if necessary as to examine or fix a found defect or a found anomaly.

According to a preferred embodiment, the testing arrangement comprising at least a first and a second inspection device according to an embodiment described in this document. The second inspection device is thereby preferably configured to move dissociated from the first inspection device (and possible from a laying head) on and/or above one or more material layer(s) and/or a surface of the component. The two inspection devices may be controlled by a common or by separate controlling unit(s). The inspection devices may be hierarchically equally arranged or the second inspection device may be hierarchically subordinated to the first one. A sensor system comprised by the second inspection device may at least in part comprise similar or different sensors as the sensor system of the first inspection device. The second inspection device may be of equal or different size compared to the first one, and/or it may comprise at least a same or a different movement mechanism compared to the first one. The first and the second inspection device may be configured to move in different zones in the forming tool, respectively. The first and the second inspection device may cooperate for examination of the material layer or of the surface of the component, for example in that the first inspection device introduces signals, sound, and/or temperature into the component and in that the second inspection device measures the respective propagation, transmission, attenuation, and/or reflection within the component.

By using multiple inspection devices, the controlling of the automated layer laying process may be accelerated. Furthermore, the examination may take place with respect to different aspects. Thus, defects may be reliably recognized.

The description additionally relates to a device for automated manufacturing of a fiber reinforced plastic laminate, which device comprises a forming tool, a laying head for automated laying of material layers in the forming tool and a testing arrangement according to one of the embodiments described herein.

In the following, a preferred embodiment is described in more detail with reference to a drawing. It should be understood that the schematically represented single elements and components may also be combined and/or formed in another manner as shown and that the device or testing arrangement is not limited to the shown embodiment.

BRIEF DESCRIPTION OF THE DRAWINGS

In the figures, schematically:

FIGURE shows an exemplary device for automated manufacturing of a fiber reinforced plastic laminate with a testing arrangement according to an embodiment.

DETAILED DESCRIPTION

A device 100 for automated manufacturing of a fiber reinforced plastic laminate with a testing arrangement is shown in the FIGURE.

The device 100 comprises a forming tool 110 in which a laying head 120 lays stripped material layers 30 in an automated manufacturing process. In this manner, a component made of fiber reinforced plastic is manufactured.

The testing arrangement comprises an inspection device 10 with a sensor system 11. The inspection device 10 moves above the respective laid material layers 30 as to examine these by means of the sensor system 11 section by section and, thus, to check it for defects. For movement, the inspection device of the shown example comprises a hover mechanism 13 which is schematically represented as a rotor; alternatively or additionally, the hover mechanism may comprise, for example, a suspension, an air cushion mechanism, and/or a magnetic levitation mechanism.

The testing arrangement further comprises a controlling unit 12 which, in the present example, controls operations of the inspection device 10 (e.g., its movement and/or operations of the sensor system) from external outside of the forming tool 110. The controlling unit 12 is stationary, in particular. Inspection device and controlling unit comprise (preferably wireless) means of communication which are not shown and by means of which these elements can communication with each other. As already described, the controlling unit may alternatively be attached to the inspection device 10 or may be arranged on it. In particular, the testing device may thus be configured to move in its entirety above and/or on the material layers. The testing device may here be designed as an autonomous mobile robot which is configured to control automated layer laying processes.

In the shown example, the controlling unit 12 comprises operating elements 12a by means of which an operator may take influence to the operations of the inspection device 10; for example, the operator may select operations shown in a selection menu 17. Alternatively or additionally, the inspection device 10 may be controlled automated. In particular, the testing arrangement may comprise its own artificial intelligence and may act autonomously.

The sensor system 11 is configured to examine the material layers 30. The sensor system may generate and measure light or heat reflections locally defined, and/or create images of sections of the material layers 30.

In the example shown in the drawing, the inspection device 10 has found a defect 20 in the material layers 30 and provides a signal 14 as to show the finding to an operator. The signal may be, for example, an acoustic alarm, and/or comprise image signals based on which a display device 16 generates an image of the defect 20 in the material layers.

The shown inspection device 10 exemplarily further comprises a gripper 15 by means of which contaminants on the material layers can be removed and, thus, an according defect can be cleared; as described, the inspection device may alternatively or additionally comprise one or more other actuators for removing a defect, as for example at least one knife, at least one scissors, at least one magnet, laser, vacuum element, and/or gripper and/or at least one spray nozzle for additional matrix material.

The shown testing arrangement further comprises a position system 18a, 18b which is schematically shown in the drawing as measuring grid 18a at the forming tool and as position sensor 18b at the inspection device; the position sensor 18b is thereby configured to detect the position of the inspection device relative to the measuring grid 18a. Thus, when finding a defect 20, its position may also be detected, in particular. For example, based on the detected position, a map of the material surface with delineated defects may be created, and/or an additional inspection device for more detailed analysis and/or removal of the defect may be moved to the defect; alternatively or additionally, the repairing device may be moved to the defect, wherein the repairing device is configured to clear or remove the defect.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

LIST OF REFERENCE SIGNS 10 inspection device
11 sensor system
12 controlling unit
12a operating element
13 hover mechanism
14 signal
15 gripper
16 display device
17 selection menu
18a, 18b position system
20 defect
30 material layer
100 manufacturing device
110 forming tool

The invention claimed is:

1. A testing arrangement for controlling a manufacturing of a fiber reinforced component, wherein the testing arrangement comprises:
an inspection device with a sensor system, the inspection device being configured to move on and/or above one or more material layer(s) and/or a surface of the component and to examine the material layer(s) or the surface with the sensor system,
wherein the inspection device is configured to move in a forming tool dissociated or separated from a laying head which lays the material layers in an automated layer laying process, and
wherein the inspection device is configured to change its direction of movement relative to a direction of movement of the laying head, and
wherein the inspection device comprises at least one actuator for removing a defect.

2. The testing arrangement according to claim 1, further comprising at least one controlling unit configured to control the movement of the inspection device and/or the activities of the sensor system.

3. The testing arrangement of claim 2, wherein the controlling unit:
is configured to operate being stationary arranged; or is arranged on or at the inspection device and being configured to move with the inspection device; or is configured to move dissociated from the inspection device.

4. The testing arrangement of claim 1, wherein the inspection device comprises wheels, stilts, at least one suspension and/or at least one hover mechanism representing a moving mechanism.

5. The testing arrangement of claim 1, wherein the sensor system is configured to apply one or more of:

thermography method, laser light sectioning method, stray light method, laser time-of-flight measurement, image recognition, pattern recognition, magnetic resonance method, triangulation method for examination of the material layer(s) or of the surface.

6. The testing arrangement of claim 1, being configured to examine the material layer(s) or the surface of the component for defects based on the examination by the sensor system.

7. The testing arrangement of claim 6, being configured to generate at least an optical and/or acoustical signal;

cancel a process step of the manufacturing;
fix the defect;
mark the defect on the material layer(s); and/or
store data of a position of the defect,
in case of finding a defect.

8. The testing arrangement of claim 1, further comprising a position system for determining a position of the inspection device at or above the material layer(s).

9. The testing arrangement of claim 1, further comprising a display device configured to graphically display results of the testing arrangement.

10. The testing arrangement of claim 1, wherein the inspection device is configured to communicate with at least one element for manufacturing the component and/or with a repairing device for material layers.

11. The testing arrangement of claim 1, wherein the inspection device is a first inspection device and wherein the testing arrangement further comprises at least one second inspection device with a second sensor system, wherein the second inspection device is controlled by a controlling unit commonly with the first inspection device or by another controlling unit as the first inspection device;

wherein the second sensor system comprises at least one other sensor and/or applies another measuring method as the sensor system of the first inspection device;

wherein the second inspection device comprises a different or an equal movement mechanism in comparison to the first inspection device; and/or wherein the first inspection device is configured to communicate with the second inspection device.

12. A device for automated manufacturing of a fiber reinforced plastic laminate, the device comprising:

a forming tool;

a laying head for automated laying of material layers in the forming tool; and a testing arrangement for controlling a manufacturing of a fiber reinforced component, wherein the testing arrangement comprises an inspection device with a sensor system, which inspection device is configured to move on and/or above one or more material layer(s) and/or a surface of the component and to examine the material layer(s) or the surface with the sensor system, wherein the forming tool is dissociated or separated from the laying head and comprises the inspection device, and wherein the inspection device is configured to change its direction of movement relative to a direction of movement of the laying head, and wherein the inspection device comprises at least one actuator for removing a defect.

* * * * *